(12) United States Patent
Hall et al.

(10) Patent No.: US 10,444,144 B2
(45) Date of Patent: Oct. 15, 2019

(54) IDENTIFICATION OF CONSUMED DRUGS AND FOOD BY UNIQUE NEAR INFRARED TAG LIBRARIES

(71) Applicants: David R. Hall, Provo, UT (US); Dan Allen, Springville, UT (US); Daniel Hendricks, Provo, UT (US); Andrew Nguyen, Provo, UT (US); Conrad Rosenbrock, Provo, UT (US); Travis Niederhauser, Mapleton, UT (US); Joe Fox, Spanish Fork, UT (US); Terrece Pearman, Draper, UT (US); Steven J. M. Butala, Provo, UT (US)

(72) Inventors: David R. Hall, Provo, UT (US); Dan Allen, Springville, UT (US); Daniel Hendricks, Provo, UT (US); Andrew Nguyen, Provo, UT (US); Conrad Rosenbrock, Provo, UT (US); Travis Niederhauser, Mapleton, UT (US); Joe Fox, Spanish Fork, UT (US); Terrece Pearman, Draper, UT (US); Steven J. M. Butala, Provo, UT (US)

(73) Assignee: Hall Labs LLC, Provo, UT (US)

( * ) Notice: Subject to any disclaimer, the term of this patent is extended or adjusted under 35 U.S.C. 154(b) by 287 days.

(21) Appl. No.: 15/493,433

(22) Filed: Apr. 21, 2017

(65) Prior Publication Data
US 2018/0306824 A1 Oct. 25, 2018

(51) Int. Cl.
*G01N 21/359* (2014.01)
*A61B 10/00* (2006.01)
(Continued)

(52) U.S. Cl.
CPC .......... *G01N 21/359* (2013.01); *A61B 5/145* (2013.01); *A61B 10/007* (2013.01);
(Continued)

(58) Field of Classification Search
CPC combination set(s) only.
See application file for complete search history.

(56) References Cited

U.S. PATENT DOCUMENTS

2015/0273063 A1\* 10/2015 Keller .................... G01N 33/94
424/10.1

OTHER PUBLICATIONS

Landau et al. (J. Agric. Food Chem., 2002, 50:1374-1378) (Year: 2002).\*

(Continued)

*Primary Examiner* — Jeremy C Flinders

(57) ABSTRACT

We disclose a method of tagging nutritional or drug compositions using chemical entities which are known to be safely consumed and which are detectable using known techniques, including near IR spectroscopy. The chemical entities used as tags may be detected in easily obtainable biological samples, including urine and feces. The biological sample may be deposited into a medical toilet which may analyze the biological sample using an analytical device associated with the medical toilet. The tag may be identified and quantified to then identify and quantify the nutritional or drug composition the subject consumed along with the tag. This system may be used to track the source of a food or drug, confirm compliance to a prescribed diet or drug treatment, confirm drug consumption in clinical trials, identify the source of contaminated food, and identify the food substances used to produce food products.

20 Claims, 6 Drawing Sheets

(51) Int. Cl.
*G01N 33/15* (2006.01)
*A61B 5/145* (2006.01)
*G01N 30/02* (2006.01)

(52) U.S. Cl.
CPC ......... *A61B 10/0051* (2013.01); *G01N 33/15* (2013.01); *A61B 10/0038* (2013.01); *A61B 2010/0009* (2013.01); *A61B 2010/0061* (2013.01); *A61B 2010/0077* (2013.01); *A61B 2010/0087* (2013.01); *G01N 30/02* (2013.01); *G01N 2458/15* (2013.01)

(56) References Cited

OTHER PUBLICATIONS

Shaw et al. (Encyclopedia of Analytical Chemistry, 2008, pp. 1-24) (Year: 2008).*

* cited by examiner

| Name | Structure |
|---|---|
| Polyethylene Glycol | 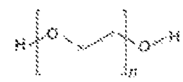 |
| Ethylene Vinyl Acetate | 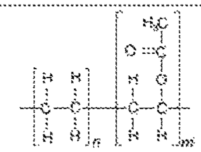 |
| Providone | 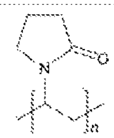 |
| Copovidone | 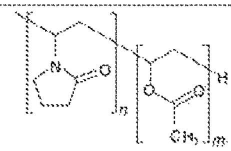 |
| Propylparaben | 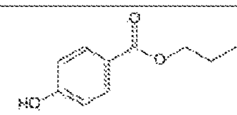 |
| Methylparaben | 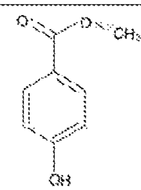 |
| Sucralose | 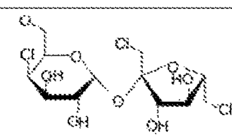 |
| Acesulfame K | 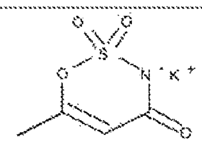 |
| Sorbitol | 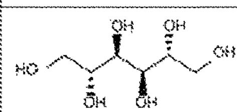 |
| Mannitol | 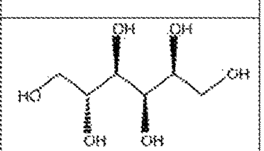 |
| Xylitol | 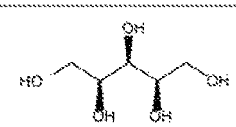 |

FIG. 1

| Name | Structure |
|---|---|
| Steviol Glycoside | 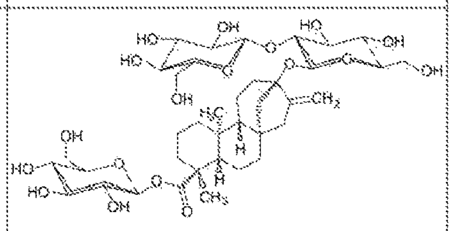 |
| Riboflavin | 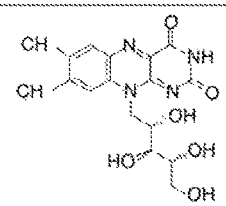 |
| Oleic Acid | 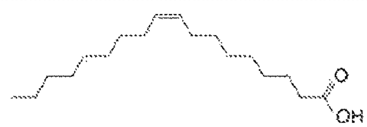 |
| Tartaric Acid | 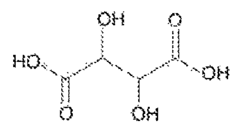 |
| 1, 8-eucalyptol | 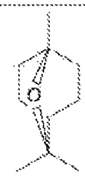 |
| Trans-anethole | 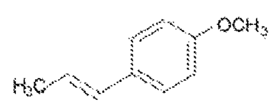 |
| Limonene-2D | 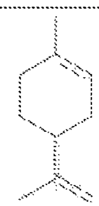 |
| Linalool | 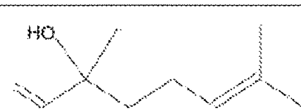 |
| Citronellol | 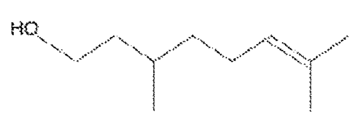 |

| Name | AVG MW (g/mol) | Example MW Range (g/mol) |
|---|---|---|
| PEG 400 | 400 | 380-420 |
| PEG 600 | 600 | 570-630 |
| PEG 800 | 800 | 720-880 |
| PEG 1000 | 1000 | 950-1050 |
| PEG 1500 | 1500 | 1300-1650 |
| PEG 2000 | 2000 | 1900-2200 |

FIG. 4

IDENTIFICATION OF CONSUMED DRUGS AND FOOD BY UNIQUE NEAR INFRARED TAG LIBRARIES

BACKGROUND

Field of the Invention

This disclosure relates to methods of tracking and identifying foods and pharmaceuticals after consumption, particularly by screening biological samples for food and drug tags.

Background of the Invention

The consumption of drugs is largely untracked. This is problematic when dealing with issues that include drug addiction, drug compliance, and dosing control and adjustment. For example, it is difficult to assess whether an individual who is being treated with opioid replacement therapy (ORT) while being weaned off opioid use is consuming the prescribed longer acting but less euphoric opioid or has relapsed into using the drug of abuse. It is also difficult to interpret clinical studies when drug compliance of study subjects is inconsistent.

Furthermore, the consumption of food and other nutritional compounds is often desirable. This may be useful to confirm adherence to a prescribed diet or to confirm the source of food products. Often, it is useful to identify the source of food after a subject has consumed the food. For example, when a subject becomes ill and it is suspected that the cause is consumption of contaminated food, it may be desirable to identify the source of the food the subject consumed. In another example, when a food source that is used as an ingredient in other food products has been found to be contaminated, it is desirable to identify the downstream food products that were prepared using the contaminated batch of the original food source. In this example, only the downstream food products made from the contaminated food source may need to be destroyed while other batches of the product may be salvaged for safe use.

Furthermore, a contaminated original food source may be used to produce may different downstream food products. If multiple subjects become ill from consuming contaminated food products, the source of the illnesses may be identified by identifying a common original food source consumed by each subject, even though not all the subjects consumed the same end food product. In addition, the illness may be a reaction to a food allergy and the diagnosis may be made by identifying the components of the food product.

Tracking of food and drugs in the easily accessible biological samples is desirable, particularly when little or no sample processing is required. Tracking molecules with a known safety record are also desirable. A tracking molecule that is commonly added to food or pharmaceutical products and which has been studied with regard to its pharmacokinetics, stability, metabolism, and adverse effects would be an attractive candidate. In addition, a tracking molecule that may be detected in the human waste stream using noninvasive and well-established analytical methods would be useful.

BRIEF SUMMARY OF THE INVENTION

We disclose a system of identifying drug compositions or nutritional compositions which a subject has consumed by analyzing a biological sample collected from the subject. The system includes unique tags which are applied to or mixed with the drug compositions or nutritional compositions prior to consumption. The tags may include one or more chemicals which may be detectable in the biological sample. The tag may include multiple chemicals which may be applied to or mixed with the drug composition or nutritional composition in a unique ratio.

The unique tags may be detected using a variety of analytical techniques, including near infrared (hereinafter, near IR) spectroscopy, other methods of detecting electromagnetic signatures, various forms of chromatography, electrophoresis techniques, or combinations thereof. The analytical device used to detect the unique drug tags may be connected to or within a medical toilet. The medical toilet may also collect other health metrics that may be combined with the information obtained by detecting the unique tags to provide a more complete assessment of the subject's health.

The biological sample may be one that is conveniently obtained, including urine or feces. In other embodiments, the biological sample may include whole blood, serum, plasma, cerebrospinal fluid, ascites, mucous, gastric gavage, breath, saliva, or breast milk.

Examples of chemicals that may be included in the disclosed tags include polyethylene glycol (hereinafter, PEG), ethylene-vinyl acetate, copovidone, povidone, propylparaben, methyl paraben, sucralose, acesulfame potassium, mannitol, sorbitol, xylitol, linalool, and citronellol.

In some embodiments, the tags may include PEGS of average molecular weights of about 400 g/mol to about 2000 g/mol. In some embodiments, the tags may include povidone monomers of about 25, about 30, or about 90.

The unique tags may be identified and quantified and the data may then be extrapolated to identify the associated drug composition or nutritional composition. Tracking the sources of drug compositions and nutritional compositions may be used to solve the problems discussed in the Background section above.

BRIEF DESCRIPTION OF THE DRAWINGS

FIG. 1 is a table showing the names and chemical structures of minimally metabolized and chemically stable molecules which may be included in tags according to the disclosure.

FIG. 4 is a table showing variations of polyethylene glycol molecules which may be included in tags according to the disclosure.

DETAILED DESCRIPTION OF THE INVENTION

Definitions

Figure 2:
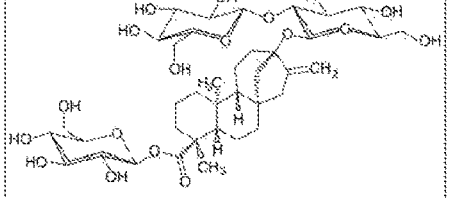
FIG. 2 is a table showing the names and chemical structures of partially metabolized or less stable molecules which may be included in tags according to the disclosure.
Figure 2:
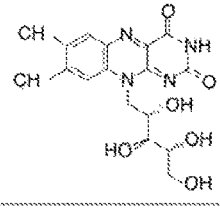
Figure 2:
Figure 2:
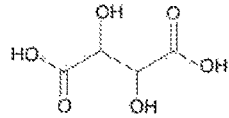
Figure 2:
Figure 2:
Figure 2:
Figure 2:
Figure 2:

Drug, as used herein, means any pharmacologically active agent or mixture of agents.

Drug consumption, as used herein, means taking a drug into the body through any method of administration, including orally, intravenously, intraarterially, intraperitoneally, sublingually, trans-dermally, trans-mucousally, via suppositories, through inhalants, or any other method of drug administration known in the art.

Nutritional composition, as used herein, means a food substance or nutritional supplement, either liquid or solid, which provides nutrients used for the maintenance, growth, reproduction, health, and disease prevention of a subject.

Biological sample, as used herein, means urine, feces, whole blood, serum, plasma, cerebrospinal fluid, ascites, mucous, gastric gavage, breath, saliva, breast milk, or any combination thereof.

Subject, as used herein, means a patient, a participant in a medical study, or any individual who has consumed a nutritional composition or drug composition which includes a tag as described herein.

Nutritional composition consumption, as used herein, means taking a nutritional composition into the body through any method of administration, including orally, intraperitoneally, intravenously, intraarterially, or through a nasogastric tube.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a system for identifying and tracking consumed nutritional and drugs compositions in a biological sample produced by a subject who has consumed the nutritional or drug composition. In this system, a nutritional or drug composition may be tagged with at least one chemical which may be used as a unique tag and which may be detected in a biological sample. In some embodiments, the chemical may be detected by near IR spectroscopy. The chemical may also be detectable by other methods of detecting electromagnetic signatures, various forms of chromatography, electrophoresis techniques, or combinations thereof. Examples include, but are not limited to gas chromatography-mass spectrometry, liquid chromatography, capillary zone electrophoresis with ultraviolet (hereinafter, UV) absorbance, high performance liquid chromatography with UV absorbance, reverse-phase chromatography, fluorescence spectroscopy, high performance thin layer chromatography, infrared spectroscopy, UV spectroscopy, nuclear magnetic resonance, ion mobility spectrometry, liquid chromatography-ion mobility spectroscopy, liquid chromatography-electrochemical detection, liquid chromatography-UV spectroscopy with a normal UV photodetector, thin layer chromatography, liquid chromatography, and Raman spectroscopy.

In some embodiments, the subject has consumed more than one drug composition, more than one nutritional composition, or a combination of one or more drug compositions and one or more nutritional compositions. Each nutritional or drug composition may include at least one unique tag as disclosed herein. Each unique tag may comprise of a single chemical or multiple chemicals which may be present in defined ratios. The defined ratio may, in fact, be part of the tag by providing information about the tagged composition. For example, different nutritional or drug compositions may be tagged with the same two chemicals which may be present in different ratios, thus making the tags unique.

Examples of chemicals which may comprise the unique tags include, but are not limited to, PEG, ethylene-vinyl acetate, copovidone, povidone, propylparaben, methyl paraben, acesulfame potassium, mannitol, sorbitol, xylitol, steviol glucuronide, sucralose, oleic acid, trans-anethole, 1,8-eucalyptol, limonene-2D, linalool, citronellol, riboflavin, tartaric acid, and salts of tartaric acid. Trans-anethole is a component of anise oil, 1,8-eucalyptol is a component of eucalyptus oil, and limonene-2D is a component of orange oil. Linalool is a component of coriander oil and citronellol is a component of rose oil or geranium oil. Consequently, the unique tags may include anise oil, eucalyptus oil, orange oil, coriander oil, rose oil, and germanium oil.

The PEG molecules which may be included in tags according to the disclosure may be of an average molecular weight of between about 400 g/mol and about 2000 g/mol. For example, the average molecular weight of the PEG molecules which may be included in the tag may be about 400, about 600, about 800, about 1000, about 1500, and/or about 2000. PEGs of these molecular weights are detectable using known techniques, including near IR spectroscopy, and are excreted in bodily waste, including urine. In addition, unlike PEGS of larger molecular weights, these smaller PEGs do not act as a laxative.

In some embodiments, the povidone molecules which may be included in tags according to the disclosure may be monomers of about 25, about 30, about 90, or combinations thereof.

The biological sample which may be analyzed to detect and identify the tags disclosed herein may include urine, feces, whole blood, serum, or plasma. In addition, the biological sample may comprise of cerebrospinal fluid, ascites, mucous, gastric gavage, saliva, breath, or breast milk. In some examples, the biological sample may require sample preparation prior to analysis to detect and identify the unique tag. In some embodiments, for example detecting PEG in urine, no sample preparation may be required.

In some embodiments, the at least one unique tag in the biological sample may be quantified. In some embodiments, the method of quantification may include applying the analytical result to a standard curve. For example, in embodiments in which the biological sample is analyzed using near IR spectroscopy, the intensity of the near IR spectra reading obtained from the biological sample analysis may be applied to a standard curve created by measuring chemicals used to create drug tags using near IR spectroscopy. Another quantification method may include the method of standard addition where the matrix (biological sample) may present significant interference making accurate quantification difficult. In this method, known amounts of analyte are added and measurements performed. The resultant linear line is then extrapolated to zero to determine the original amount of analyte in the sample.

In some embodiments, the biological sample may be analyzed using a medical toilet. The medical toilet may include an analytical device, for example, a spectrometer, which may analyze biological samples. In some embodiments, the spectrometer included in the medical toilet may conduct measurements in the near IR range. In some embodiments, the medical toilet may include devices which may collect other metrics relevant to the subject's health and physiological state. The information from these devices may be combined with the data obtained from analyzing the disclosed tags to provide a thorough health assessment of the subject.

In some embodiments, the process of measuring the unique tags in a subject's biological sample may be performed multiple times. The data collected from these multiple analyses may be used to perform a trending analysis.

Accordingly, the discloses system may be used to assess the subject's food and drug consumption habits over time.

Referring now to the drawings, FIG. 1 provides a table which lists examples of chemical entities which may be included in tags according to the disclosure along with their chemical structures. These include polyethylene glycol, ethylene-vinyl acetate, copovidone, povidone, propylparaben, methyl paraben, sucralose, acesulfame potassium, mannitol, sorbitol, and xylitol. The compounds in the table of FIG. 1 are relatively stable over time.

FIG. 2 provides a table which lists additional examples of chemical entities which may be used as tags according to the disclosure along with their chemical structures. These include steviol glucuronide, oleic acid, trans-anethole, 1,8-eucalyptol, limonene-2D, riboflavin, tartaric acid, salts of tartaric acid, linalool, and citronellol. These chemical entities are less stable over time than those presented in FIG. 1 so may be used within a defined amount of time after applying the tag to the drug composition or nutritional composition. In addition, the chemicals in the table of FIG. 2 may be metabolized such that only a fraction of the chemical used in the tag may be excreted intact. Consequently, metabolites of the chemicals may be measured or the original amount of the tag may be calculated based on known or measured metabolism rates.

Figure 3:
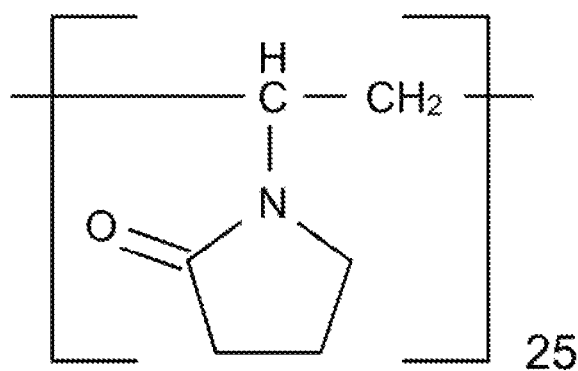
FIG. 3 shows three variations of povidone which may be included in tags according to the disclosure.
Figure 3:
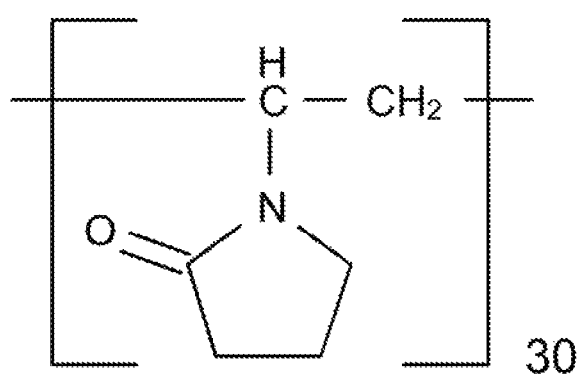
Figure 3:
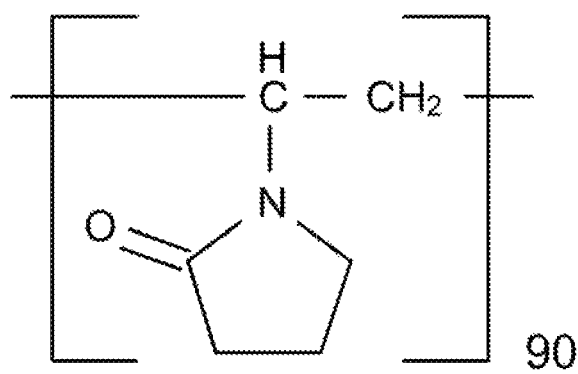

FIG. 3 shows three forms of povidone which may be used as tags according to the disclosure. These include polymers of varying sizes including a 25-mer, a 30-mer, and a 90-mer.

FIG. 4 provides a table which lists examples of PEG polymers of varying average molecular weights. These include PEG 400, PEG 600, PEG 800, PEG 1000, PEG 1500, and PEG 2000. Polyethylene glycol is a polymer made of varying numbers of monomers and each polyethylene glycol solution may be comprised of a range of molecular weights, depending on the number of monomers in the polymers, with an average molecular weight. Examples of the ranges which may be included in a source of PEGs is shown in the table of FIG. 4.

Figure 5:
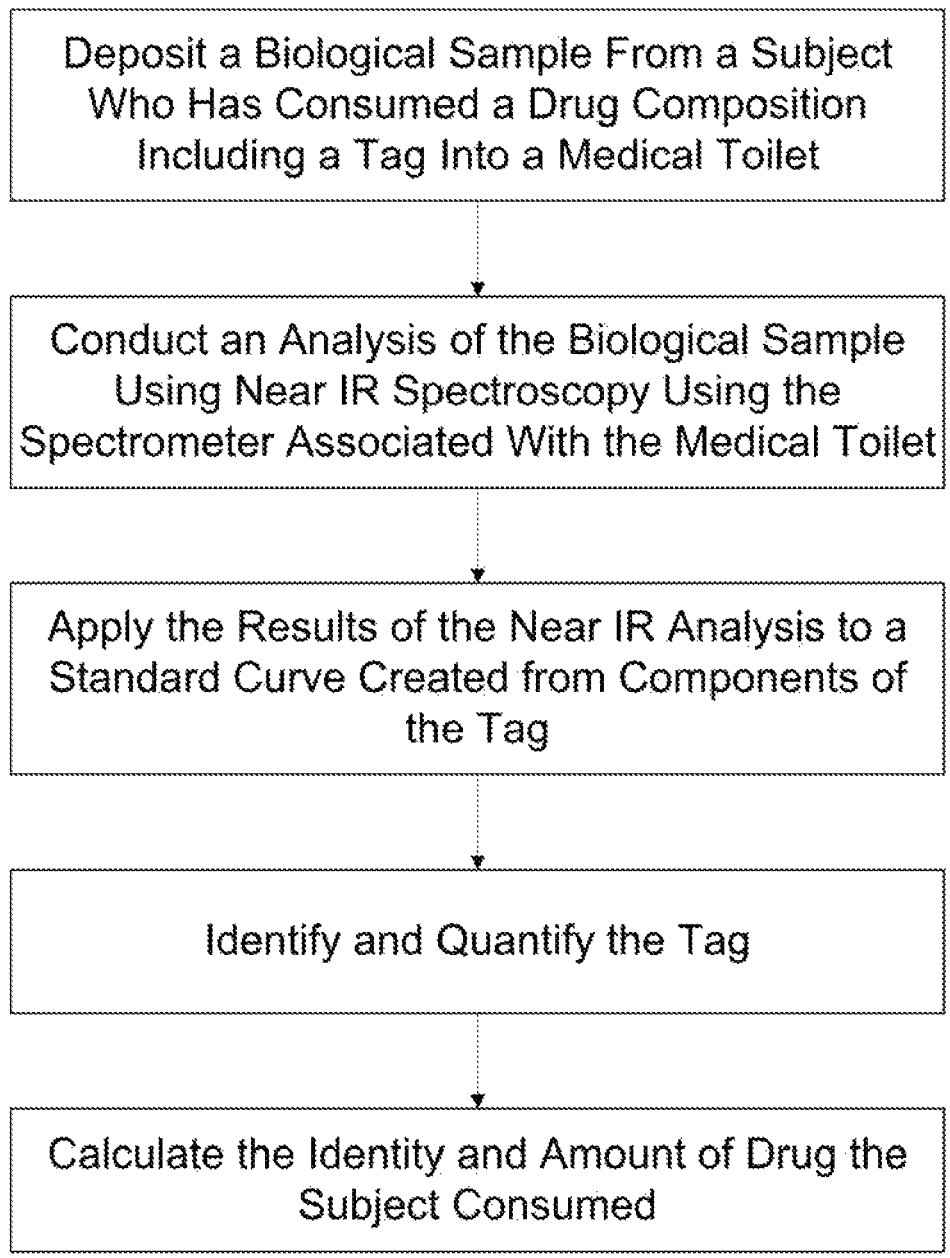
FIG. 5 provides a flow chart which includes steps which may be used in performing an embodiment of a method of using the disclosed tagging system to identify a drug consumed by a subject.

FIG. 5 is a flow chart illustrating a series of steps which may be performed to identify and quantify a drug composition using the disclosed tagging system. In this example, the biological sample may be analyzed using a medical toilet. A biological sample is deposited into the medical toilet for analysis. The biological sample may be produced by a subject who has consumed a drug composition that includes a tag as disclosed herein. The biological sample may be analyzed by near IR spectroscopy. In this example, the spectrometer may be associated with the medical toilet. The results of the near IR spectroscopy analysis of the biological sample may be applied to a standard curve. The standard curve may be created using an analysis of varying quantities or concentrations of the one or more chemical entities in the tag. The near IR spectroscopy analysis and its application to the standard curve may be used to identify and quantify the one or more chemical entities in the tag which may then be used to extrapolate the identity and quantity of the drug composition the subject consumed.

Figure 6:
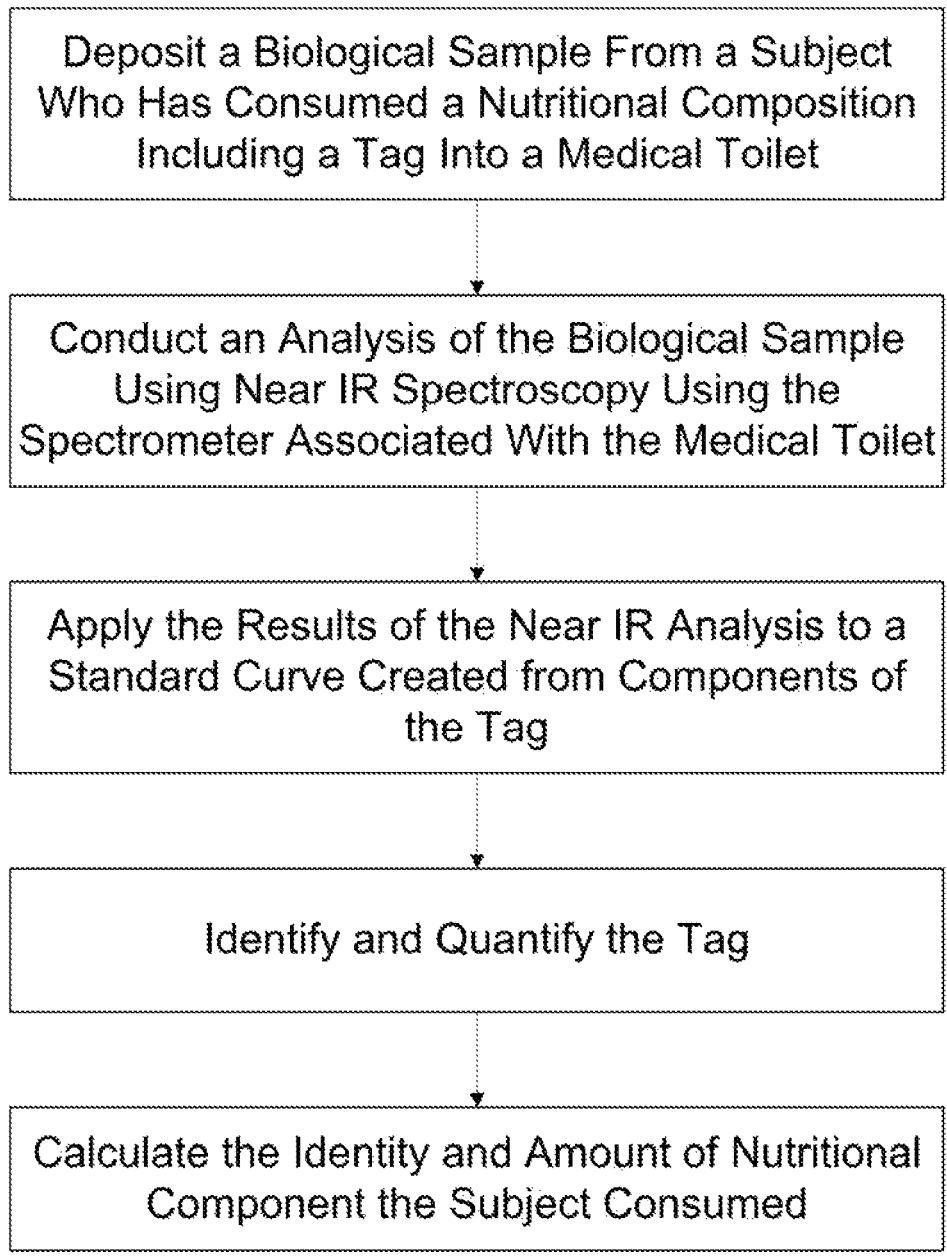
FIG. 6 provides a flow chart which includes steps which may be used in performing an embodiment of a method of using the disclosed tagging system to identify a food consumed by a subject.

FIG. 6 is a flow chart illustrating a series of steps which may be performed to identify and quantify a nutritional composition using the disclosed tagging system. In this example, the biological sample may be analyzed using a medical toilet. A biological sample is deposited into the medical toilet for analysis. The biological sample may be produced by a subject who has consumed a nutritional composition that includes a tag as disclosed herein. The biological sample may be analyzed by near IR spectroscopy. In this example, the spectrometer may be associated with the medical toilet. The results of the near IR spectroscopy analysis of the biological sample may be applied to a standard curve. The standard curve may be created using an analysis of varying quantities or concentrations of the one or more chemical entities in the tag. The near IR spectroscopy analysis and application to the standard curve may be used to identify and quantify the one or more chemical entities in the tag which may then be used to extrapolate the identity and quantity of the nutritional composition the subject consumed.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A method of tracking a consumed substance comprising the steps of:
   a. analyzing a biological sample using a near infrared spectroscopy technique, wherein the biological sample is obtained from a subject who has consumed at least one drug composition, and wherein each of the at least one drug composition comprises at least one drug and at least one unique tag, and wherein the at least one unique tag is detectable by near infrared spectroscopy;
   b. identifying the presence of the at least one unique tag in the biological sample; and
   c. extrapolating the identification of the at least one unique tag to identify the consumed drug composition.

2. The method of claim 1, wherein the at least one unique tag comprises one or more of polyethylene glycol, ethylene-vinyl acetate, copovidone, povidone, propylparaben, methyl paraben, acesulfame potassium, mannitol, sorbitol, xylitol, steviol glucuronide, sucralose, oleic acid, trans-anethole, 1,8-eucalyptol, limonene-2D, linalool, citronellol, riboflavin, tartaric acid, and salts of tartaric acid.

3. The method of claim 2, wherein the at least one unique tag comprises polyethylene glycol, and wherein the polyethylene glycol comprises polymers of one or more of the following average molecular weights: 400, 600, 800, 1000, 1500, and 2000.

4. The method of claim 2, wherein the at least one tag comprises polyethylene glycol, and wherein the polyethylene glycol comprises polymers of an average molecular weight of between about 400 and about 2000.

5. The method of claim 2, wherein the at least one unique tag comprises povidone, and wherein the povidone comprises one or more of the following number of monomers: 25, 30, and 90.

6. The method of claim 1, wherein the biological sample consists of one or more of the following: urine, feces, whole blood, serum, plasma, cerebrospinal fluid, ascites, mucous, gastric gavage, saliva, breath, and breast milk.

7. The method of claim 1, further comprising the step of quantifying the at least one unique tag by applying the intensity of the near infrared spectra reading to a standard curve.

8. The method of claim 1, wherein the step of analyzing the biological sample using a near infrared spectroscopy technique is performed within a medical toilet, and wherein the medical toilet comprises a spectrometer.

9. The method of claim 1, wherein steps (a), (b), and (c) are performed a plurality of times, and further comprising the step of performing a trending analysis.

10. The method of claim 1, wherein the at least one unique tag comprises a plurality of chemicals in a unique ratio.

11. A method of tracking a consumed substance comprising the steps of:
   a. analyzing a biological sample using a near infrared spectroscopy technique, wherein the biological sample is obtained from a subject who has consumed at least one nutritional composition, and wherein each of the at least one nutritional composition comprises at least one nutritional substance and at least one unique tag, and wherein the at least one unique tag is detectable by near infrared spectroscopy;
   b. identifying the presence of the at least one unique tag in the biological sample; and
   c. extrapolating the identification of the at least one unique tag to identify the consumed nutritional composition.

12. The method of claim 11, wherein at least one unique tag comprises one or more of polyethylene glycol, ethylene-vinyl acetate, copovidone, povidone, propylparaben, methyl paraben, acesulfame potassium, mannitol, sorbitol, xylitol, steviol glucuronide, sucralose, oleic acid, trans-anethole, 1,8-eucalyptol, limonene-2D, linalool, citronellol, riboflavin, tartaric acid, and salts of tartaric acid.

13. The method of claim 12, wherein the at least one unique tag comprises polyethylene glycol, and wherein the polyethylene glycol comprises polymers of one or more of the following average molecular weights: 400, 600, 800, 1000, 1500, and 2000.

14. The method of claim 12, wherein the at least one unique tag comprises polyethylene glycol, and wherein the polyethylene glycol comprises polymers of an average molecular weight of between about 400 and about 2000.

15. The method of claim 12, wherein the at least one unique tag comprises povidone, and wherein the povidone comprises one or more of the following number of monomers: 25, 30, and 90.

16. The method of claim 11, wherein the biological sample consists of one or more of the following: urine, feces, whole blood, serum, plasma, cerebrospinal fluid, ascites, mucous, gastric gavage, saliva, breath, and breast milk.

17. The method of claim 11, further comprising the step of quantifying the at least one unique tag by applying the intensity of the near infrared spectra reading to a standard curve.

18. The method of claim 11, wherein the step of analyzing the biological sample using a near infrared spectroscopy technique is performed within a medical toilet, wherein the medical toilet comprises a spectrometer.

19. The method of claim 11, wherein steps (a), (b), and (c) are performed a plurality of times, and further comprising the step of performing a trending analysis.

20. The method of claim 11, wherein the at least one unique tag comprises a plurality of tags which are present in a unique ratio.

* * * * *